United States Patent
Zhang

(10) Patent No.: US 8,444,982 B2
(45) Date of Patent: May 21, 2013

(54) ANTI-IGF-IR ANTIBODIES AND USES THEREOF

(75) Inventor: Mei-Yun Zhang, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 220 days.

(21) Appl. No.: 12/955,627

(22) Filed: Nov. 29, 2010

(65) Prior Publication Data

US 2011/0135663 A1 Jun. 9, 2011

Related U.S. Application Data

(60) Provisional application No. 61/266,681, filed on Dec. 4, 2009.

(51) Int. Cl.
*A61K 39/395* (2006.01)
*C07K 16/00* (2006.01)

(52) U.S. Cl.
USPC ............... 424/143.1; 530/387.1; 530/388.22; 530/387.9; 530/388.1; 530/387.3

(58) Field of Classification Search
None
See application file for complete search history.

(56) References Cited

PUBLICATIONS

Paul, Fundamental Immunology, 3rd edition, 1993, pp. 292-295.*
Bendig (1995) Methods: a companion methods in encymology 8: 83-93.*
MacCallum et al. (1996) J. Mol. Biol. 262: 732-745.*
Jackson-Booth, P.-G., et al. (2003). Inhibition of the Biologic Response to Insulin-like Growth Factor I in MCF-7 Breast Cancer Cells by a New Monoclonal Antibody to the Insulin-like Growth Factor-I Receptor. The Importance of Receptor Down-regulation. *Hormone and Metabolic Research*, 35: 850-856.
Zhang, M.-Y., et al. (2009). Characterization of a chimeric monoclonal antibody against the insulin-like growth factor-I receptor. *mAbs*, 1(5): 470-475.

* cited by examiner

*Primary Examiner* — Michael Pak
(74) *Attorney, Agent, or Firm* — Saliwanchik, Llyod & Eisenschenk

(57) ABSTRACT

The subject invention provides antibodies, or binding fragments thereof, that specifically bind to human IGF-IR. Also provided are nucleic acid molecules encoding the antibodies and binding fragments of the subject invention and vectors and host cells containing these nucleic acid molecules. The disclosure also provides methods of inhibiting cancer cell growth and metastasis in a mammal using the antibodies described herein, as well as compositions containing the antibodies, nucleic acid molecules encoding the antibodies, and host cells and vectors comprising the nucleic acid molecules. The disclosure also features the use of the polypeptides to detect the presence of IGF-IR in a mammal, and epitopes that can be used as cancer vaccine immunogens.

13 Claims, 2 Drawing Sheets

H10 VH (SEQ ID No: 1):
EVQLLESGAEVKRPGSSVRVSCQVS<u>GYSFTAYY</u>VSWVRQTPGHGLEWMGG<u>INPDNG
GNN</u>YAQKFHGRVTFIADESTRTVHMELRSLRSEDTAVYFC<u>AKSTSYDYDGYWYFDV</u>W
GQGTAVTVFSS

H10 VL (SEQ ID NO: 2):
ELQMTQSPSSVSASVGDRVTITCRAS<u>SSVSYLA</u>WYQQKPGKAPKLLIN<u>GTSSL</u>QSGVP
SRFSGSGSGTDFTLTISSLQPEDFATYYC<u>QQRSSYPFT</u>FGGGTKVEIKR

H10 H3 (SEQ ID No: 3): AKSTSYDYDGYWYFDV

H10 L3 (SEQ ID NO: 4): QQRSSYPFT

H10 VH DNA (SEQ ID NO: 5):
gaggtgcagctgctcgagtctggggctgaggtgaagaggcctgggtcctcggtgagagtctcctgccaagttctg<u>gttact
cattcactgcctactacg</u>tcagttgggtgcgacagacccctggacacgggcttgagtggatggg<u>agggattaatcctgaca
atggtggtaac</u>aactacgcacagaagtttcacggccgagtgacatttatcgccgacgagtccacgaggacagtccacat
ggaactgcgcagcctgagatctgaggacacggccgtctattttgt<u>gcaaagtcaacctcctatgattacgacggttactgg
tacttcgatgtc</u>tggggccaagggaccgcggtcaccgtcttctcctca

H10 VL DNA (SEQ ID NO: 6):
gagctccagatgacccagtctccatcttccgtgtctgcatctgtcggagacagagtcaccatcacttgtcgggcgagttcaa
<u>gtgtaagttact</u>tagcctggtatcagcagaaaccagggaaagcccctaagctcctgatcaat<u>ggcacgtcc</u>agtttgcaaa
gtgggggtcccatcaaggttcagcggcagtggatctgggacagatttcactctcaccatcagcagcctgcagcctgaagatt
ttgcgacttactattgt<u>cagcaaaggagtagttacccattcacg</u>ttcggcggagggaccaaggtggagatcaaacga

H10 H3 DNA (SEQ ID NO: 7): gcaaagtcaacctcctatgattacgacggttactggtacttcgatgtc

H10 L3 DNA (SEQ ID NO: 8): cagcaaaggagtagttacccattcacg

FIG. 1

ANTI-IGF-IR ANTIBODIES AND USES THEREOF

CROSS-REFERENCE TO A RELATED APPLICATION

This application claims the benefit of U.S. provisional application Ser. No. 61/266,681, filed Dec. 4, 2009, which is incorporated herein by reference in its entirety.

TECHNICAL FIELD

This disclosure pertains generally to potent neutralizing monoclonal antibodies against IGF-IR, and methods of using the same for cancer therapy.

BACKGROUND OF THE INVENTION

The insulin-like growth factors (IGFs) signaling system has been shown to play important roles in neoplasia. Insulin-receptors (IR) belong to the IGF signaling network. IGF receptor type 1 (IGF-IR) and its ligands (IGFI and II) are over-expressed in many types of solid and hematopoietic malignancies, including prostate cancer, breast cancer, liver cancer, and colon cancer, etc. There is substantial experimental and clinical evidence that targeting IGF-IR is a promising therapeutic strategy against cancer.

Strategies for down-regulating the IGF signaling system include reducing ligand bioavailability and inhibiting receptor function. Inhibition of IGF receptor function can be achieved using receptor-specific antibodies or small molecule tyrosine kinase inhibitors. Desired IGF-IR-specific neutralizing antibodies can not only inhibit IGF-IR function, but also block the IGF-IR-mediated signaling pathway. There is a need to develop IGF-IR-specific antibodies that can inhibit cell-surface IGF-IR and block the binding of IGF-IR ligands to IGF-IR, thereby inhibiting ligand-induced receptor phosphorylation and the downstream signaling. IGF-IR-specific antibodies without cross-reactivity with IR are particularly desired.

BRIEF SUMMARY OF THE INVENTION

The subject invention provides antibodies and binding fragments thereof that specifically bind to human insulin-like growth factor 1 receptor (also known as human IGF receptor type 1). In one embodiment, the subject invention provides an antibody that binds to the extracellular domain of human IGF-IR, and thereby blocks the binding of both IGF-I and -II to IGF-IR and inhibits both IGF-I and IGF-II induced phosphorylation of IGF-IR and the downstream signaling, which lead to cancer cell proliferation and metastasis. These and other advantages of the invention, as well as additional inventive features, will be apparent from the description of the invention provided herein.

In one embodiment, the subject invention provides an isolated antibody (H10), or a binding fragment thereof, comprising an amino acid sequence selected from H10 $V_H$ (SEQ ID NO: 1), H10 $V_L$ (SEQ ID NO: 2), H10 H3 (SEQ ID NO: 3), H10 L3 (SEQ ID NO: 4), or a combination thereof, wherein the antibody specifically binds to an epitope of IGF-IR.

The subject invention also includes pharmaceutical compositions comprising the antibody of the subject invention, epitopes that bind to the antibody, and methods of using the antibody to treat cancer in a mammal and to detect IGF-IR in a mammal.

Additionally, the subject invention provides an isolated nucleic acid molecule encoding the antibody of the subject invention, or a binding fragment thereof, comprising a nucleic acid sequence selected from H10 $V_H$ DNA (SEQ ID NO: 5), H10 $V_L$ (SEQ ID NO: 6), H10 H3 (SEQ ID NO: 7), H10 L3 (SEQ ID NO: 8), or a combination thereof, wherein the nucleic acid molecule is optionally in a form of a vector, wherein the nucleic acid molecule or vector is optionally contained within a host cell, wherein the antibody or binding fragment thereof specifically binds to an epitope of IGF-IR. The disclosure also provides pharmaceutical compositions containing the nucleic acid molecules or polypeptides, and methods of using the nucleic acid molecules or polypeptides, to inhibit cancer cell growth and cancer metastasis in a mammal.

To the accomplishment of the foregoing and related ends, the invention comprises the features hereinafter fully described and particularly pointed out in the claims. The following description and the annexed drawings set forth in detail certain illustrative aspects and implementations of the invention. These are indicative of, however, a few of the various ways in which the principles of the invention may be employed. Other objects, advantages, and novel features of the invention will become apparent from the following detailed description of the invention when considered in conjunction with the drawings.

BRIEF DESCRIPTION OF THE DRAWINGS

FIG. 1 illustrates amino acid sequences of various regions of the H10 antibody and nucleic acid sequences encoding these amino acid sequences. The amino acid sequences are presented from N-terminus to C-terminus (from upper left to lower right of the Figure) in accordance with convention. Sequences of HCDR1-3 and LCDR1-3 are underlined.

BRIEF DESCRIPTION OF THE SEQUENCES

Figure 2:
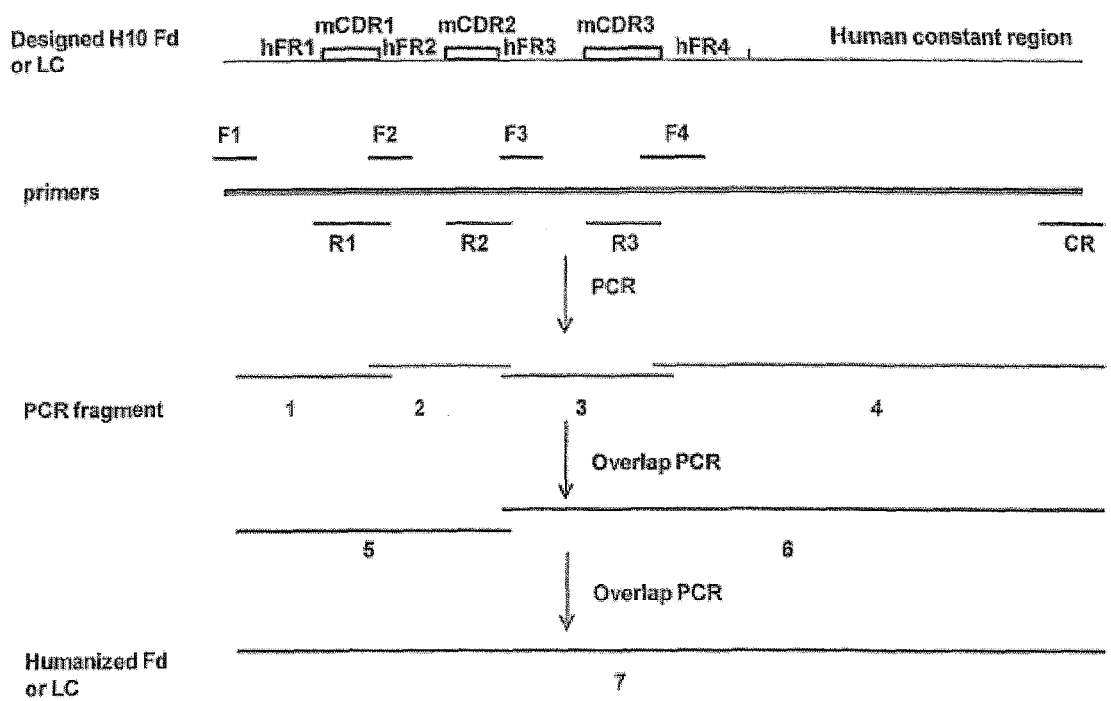
FIG. 2 is a graph that illustrates an exemplified procedure of humanizing mouse monoclonal antibody Fab m590. H: human; m: mouse.

SEQ ID NO: 1 is an amino acid sequence of a $V_H$ region of the H10 antibody of the subject invention.

SEQ ID NO: 2 is an amino acid sequence of a $V_L$ region of the H10 antibody of the subject invention.

SEQ ID NO: 3 is an amino acid sequence of an H3 region (CDR3 of a $V_H$ region) of the H10 antibody of the subject invention.

SEQ ID NO: 4 is an amino acid sequence of an L3 region (CDR3 of a $V_L$ region) of the H10 antibody of the subject invention.

SEQ ID NO: 5 is a nucleic acid sequence of a $V_H$ region of the H10 antibody of the subject invention.

SEQ ID NO: 6 is a nucleic acid sequence of a $V_L$ region of the H10 antibody of the subject invention.

SEQ ID NO: 7 is a nucleic acid sequence of an H3 region (CDR3 of a $V_H$ region) of the H10 antibody of the subject invention.

SEQ ID NO: 8 is a nucleic acid sequence of an L3 region (CDR3 of a $V_L$ region) of the H10 antibody of the subject invention.

SEQ ID NO: 9 is an amino acid sequence of CDR1 of a $V_H$ region of the H10 antibody of the subject invention.

SEQ ID NO: 10 is an amino acid sequence of CDR2 of a $V_H$ region of the H10 antibody of the subject invention.

SEQ ID NO: 11 is an amino acid sequence of CDR1 of a $V_L$ region of the H10 antibody of the subject invention.

SEQ ID NO: 12 is a nucleic acid sequence of CDR1 of a $V_H$ region of the H10 antibody of the subject invention.

SEQ ID NO: 13 is a nucleic acid sequence of CDR2 of a $V_H$ region of the H10 antibody of the subject invention.

SEQ ID NO: 14 is a nucleic acid sequence of CDR1 of a $V_L$ region of the H10 antibody of the subject invention.

SEQ ID NO: 15 is an amino acid sequence of the human insulin-like growth factor 1 receptor (hIGF-IR) used according to the subject invention.

DETAILED DISCLOSURE OF THE INVENTION

The subject invention provides antibodies, or binding fragments thereof, that specifically bind to an epitope of the type 1 insulin-like growth factor receptor (IGF-IR). The disclosure more specifically provides antibodies, or binding fragments thereof, that bind to the extracellular domain of IGF-IR. Additionally, the disclosure provides epitopes that are recognized by the polypeptides (e.g., antibodies or binding fragments thereof) described herein, which epitopes can be used, in an embodiment in the development of cancer vaccine immunogens for the treatment of cancer.

The anti-IGF-IR antibodies can be used for cancer therapy, as well as to detect IGF-IR in an animal, including without limitation a human. The anti-IGF-IR antibodies of the subject invention can also be used to detect IGF-IR in a test sample. The test sample can be a tissue sample, a biopsy sample, and the like.

In one embodiment, the anti-IGF-IR antibody specifically binds to human insulin-like growth factor I receptor (also known as human insulin-like growth factor receptor type 1 (IGF-IR)). In a specific embodiment, the human IGF-IR has an amino acid sequence of SEQ ID NO: 19 (GenBank Accession No. P08069; GI: 124240). In an embodiment, the anti-IGF-IR antibody of the subject invention specifically binds to human IGF-IR expressed on cancer cells, such as for example, SKOV-3 and MCF-7 cells. In an embodiment, the anti-IGF-IR antibody of the subject invention specifically binds to human IGF-IR expressed on IGF-IR stably transfected Hela cells.

The term "binding specificity," "specificity," "specifically reacts," or "specifically interacts," as used herein, refers to the ability of an antibody or other agent to detectably bind an epitope presented on an antigen, such as an epitope of IGF-IR, while having relatively little detectable reactivity with other proteins or structures. Specificity can be relatively determined by binding or competitive assays, using e.g., Biacore instruments. Specificity can be exhibited by, e.g., an about 10:1, about 20:1, about 50:1, about 100:1, about 10,000:1 or greater ratio of affinity/avidity in binding to the specific antigen versus nonspecific binding to other irrelevant molecules.

In one embodiment, the disclosure provides an isolated polypeptide (e.g., antibody, or a binding fragment thereof), comprising the amino acid sequence selected from H10 $V_H$ (SEQ ID NO: 1), H10 $V_L$ (SEQ ID NO: 2), H10 H3 (CDR3 of a $V_H$ region) (SEQ ID NO: 3), H10 L3 (CDR3 of a $V_L$ region) (SEQ ID NO: 4), or a combination thereof, wherein the polypeptide binds to an epitope of IGF-IR ectodomain. The polypeptide can comprise sequences selected from (a) the amino acid sequences of SEQ ID NO: 1 and SEQ ID NO: 2; (b) the amino acid sequences of SEQ ID NO: 3 and SEQ ID NO: 4; (c) the amino acid sequences of SEQ ID NO: 1 and SEQ ID NO: 4; or (d) the amino acid sequences of SEQ ID NO: 2 and SEQ ID NO: 3.

In an embodiment, CDR1 of a $V_H$ region of the anti-IGF-IR antibody comprises SEQ ID NO: 9. In an embodiment, CDR2 of a $V_H$ region of the anti-IGF-IR antibody comprises SEQ ID NO: 10. In an embodiment, CDR3 of a $V_H$ region of the anti-IGF-IR antibody comprises SEQ ID NO: 3. In a specific embodiment, a $V_H$ region of the anti-IGF-IR antibody comprises SEQ ID NO: 1. In an embodiment, CDR1 of a $V_L$ region of the anti-IGF-IR antibody comprises SEQ ID NO: 11. In an embodiment, CDR2 of a $V_L$ region of the anti-IGF-IR antibody comprises GTS. In an embodiment, CDR3 of a $V_L$ region of the anti-IGF-IR antibody comprises SEQ ID NO: 4. In a specific embodiment, a $V_L$ region of the anti-IGF-IR antibody comprises SEQ ID NO: 2.

The disclosure also provides an isolated nucleic acid molecule encoding a polypeptide, or a binding fragment thereof, comprising H10 $V_H$ DNA (SEQ ID NO: 5), H10 $V_L$ DNA (SEQ ID NO: 6), H10 H3 DNA (SEQ ID NO: 7), H10 L3 DNA (SEQ ID NO: 8), or a combination thereof, wherein the nucleic acid molecule is optionally in the form of a vector, wherein the nucleic acid molecule or vector is optionally contained within a host cell. In certain embodiments, the nucleic acid molecule can encode a polypeptide comprising (a) the amino acid sequences of SEQ ID NO: 1 and SEQ ID NO: 2; (b) the amino acid sequences of SEQ ID NO: 3 and SEQ ID NO: 4; (c) the amino acid sequences of SEQ ID NO: 1 and SEQ ID NO: 4; or (d) the amino acid sequences of SEQ ID NO: 2 and SEQ ID NO: 3.

In an embodiment, CDR1 of a $V_H$ region of the anti-IGF-IR antibody is encoded by a sequence comprising SEQ ID NO: 13. In an embodiment, CDR2 of a $V_H$ region of the anti-IGF-IR antibody is encoded by a sequence comprising SEQ ID NO: 13. In an embodiment, CDR3 of a $V_H$ region of the anti-IGF-IR antibody is encoded by a sequence comprising SEQ ID NO: 7. In a specific embodiment, a $V_H$ region of the anti-IGF-IR antibody is encoded by a sequence comprising SEQ ID NO: 5. In an embodiment, CDR1 of a $V_L$ region of the anti-IGF-IR antibody is encoded by a sequence comprising SEQ ID NO: 14. In an embodiment, CDR2 of a $V_L$ region of the anti-IGF-IR antibody is encoded by a sequence comprising 5' ggcacgtcc 3'. In an embodiment, CDR3 of a $V_L$ region of the anti-IGF-IR antibody is encoded by a sequence comprising SEQ ID NO: 8. In a specific embodiment, a Vl region of the anti-IGF-IR antibody is encoded by a sequence comprising SEQ ID NO: 6. The polypeptide can be any suitable polypeptide. For example, in one embodiment, the polypeptide is an antibody. Antibodies include both polyclonal and monoclonal antibodies. In addition to intact immunoglobulin molecules, also included are fragments or polymers of those immunoglobulin molecules, and human or humanized versions of immunoglobulin molecules or fragments thereof, as long as the molecules maintain the ability to bind with an epitope of the IGF-IR. The antibodies can be tested for their desired activity using the in vitro assays described herein, or by analogous methods, after which their in vivo therapeutic and/or diagnostic activities can be confirmed and quantified according to known clinical testing methods.

In another embodiment, the polypeptide is a monoclonal antibody or a binding fragment thereof. A monoclonal antibody refers to an antibody where individual antibodies within a population are identical.

The term "polypeptide" encompasses native or artificial proteins, protein fragments and polypeptide analogs of a protein sequence. A polypeptide may be monomeric or polymeric. The term "isolated polypeptide" is a polypeptide that by virtue of its origin or source of derivation (1) is not associated with naturally associated components that accompany it in its native state, (2) is substantially free of other proteins from the same species (3) is expressed by a cell of a species different from where the protein naturally originates, or (4) does not occur in nature. A polypeptide that is chemically synthesized or synthesized in a cellular system different from the cell from which it naturally originates is also considered "isolated" from its naturally associated components. A polypeptide can also be rendered substantially free of naturally associated components by isolation, using purification techniques well known in the art.

The monoclonal antibodies can be made using any procedure known in the art. For example, monoclonal antibodies of the invention can be prepared using hybridoma methods, such as those described by Kohler et al., Nature, 256, 495-497 (1975), which is hereby incorporated by reference. The monoclonal antibodies also can be made by recombinant DNA methods, such as those described in U.S. Pat. No. 4,816,567, which is hereby incorporated by reference. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 and U.S. Pat. No. 6,096,441, both of which are hereby incorporated by reference.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in International Patent Application WO 94/29348 and U.S. Pat. No. 4,342,566, both of which are hereby incorporated by reference. Papain digestion of antibodies typically produces two identical antigen-binding fragments—Fab fragments and a residual Fc fragment. Each Fab fragment has a single antigen binding site. Pepsin treatment yields a fragment that has two antigen combining sites and is still capable of cross-linking antigen.

The disclosure encompasses chimeric antibodies and hybrid antibodies, with dual or multiple antigen or epitope specificities, single chain antibodies and fragments, such as, Fab', F(ab')2, Fab, scFv, and the like, including hybrid fragments. Such antibodies and fragments can be made by techniques known in the art and can be screened for specificity and activity according to general methods for producing antibodies and screening antibodies for specificity and activity (see, e.g., Harlow and Lane. Antibodies, A Laboratory Manual. Cold Spring Harbor Publications, New York, (1988), which is hereby incorporated by reference).

The disclosure also encompasses human antibodies and/or humanized antibodies. Many non-human antibodies (e.g., those derived from mice, rats, or rabbits) are naturally antigenic in humans and, thus, can give rise to undesirable immune responses when administered to humans. Therefore, the use of human or humanized antibodies in the methods described herein serves to lessen the chance that an antibody administered to a human will evoke an undesirable immune response.

The human antibodies and humanized antibodies described herein can be prepared by any known technique. Examples of techniques for human monoclonal antibody production include those described by Boerner et al., J. Immunol., 147(1), 86-95 (1991), which is hereby incorporated by reference. Human antibodies described herein (and fragments thereof) can also be produced using phage display libraries (see, e.g., Marks et al., J. Mol. Biol., 222, 581-597 (1991)), which is hereby incorporated by reference. The human antibodies described herein can also be obtained from transgenic animals. For example, transgenic mutant mice that are capable of producing a full repertoire of human antibodies in response to immunization have been described (see, e.g., Jakobovits et al., PNAS, 90, 2551-255 (1993); and Jakobovits et al., Nature, 362, 255-258 (1993)), all of which are hereby incorporated by reference.

Methods for humanizing non-human antibodies are known in the art. For example, humanized antibodies can be generated by substituting rodent complementarity-determining regions (CDRs) or CDR sequences for the corresponding sequences of a human antibody. Detailed procedures are disclosed in Jones et al., Nature, 321, 522-525 (1986); Riechmann et al., Nature, 332, 323-327 (1988); Verhoeyen et al., Science, 239, 1534-1536 (1988), all of which are hereby incorporated by reference.

Methods that can be used to produce humanized antibodies are also described in U.S. Pat. No. 4,816,567; U.S. Pat. No. 5,565,332; U.S. Pat. No. 5,721,367; U.S. Pat. No. 5,837,243; U.S. Pat. No. 5,939,598; U.S. Pat. No. 6,130,364; and U.S. Pat. No. 6,180,377; all of which are hereby incorporated by reference.

The polypeptides, according to the subject invention also encompass bivalent antibodies, as well as fusion molecules and conjugates with other molecules that can enhance the inhibitory effect of the polypeptide. The generation of fusion molecules (e.g., proteins) and conjugates (e.g., through physical or chemical conjugation) is within the ordinary skill in the art and can involve the use of restriction enzyme or recombinant cloning techniques (see, e.g., U.S. Pat. No. 5,314,995, which is hereby incorporated by reference).

The fusion molecule (e.g., proteins and nucleic acid molecules) or conjugate can comprise one or more of SEQ ID NOs: 1-8 in combination with any suitable second molecule. For example, the fusion molecule or conjugate can comprise one or more of SEQ ID NOs: 1-8 in combination with a neutralizing scFv antibody fragment or a Fab fragment (e.g., that binds to an epitope of IGF-IR).

Toxins are poisonous substances that usually are produced by plants, animals, or microorganisms that, in sufficient doses, are lethal. Preferred toxin for use in the fusion molecules or conjugates described herein include Pseudomonas toxin, Diphtheria toxin tetanus toxoid, ricin, cholera toxin, Shiga-like toxin (SL T-I, SL T-II, SL T-10 IIV), L T toxin, C3 toxin, Shiga toxin, pertussis toxin, tetanus toxin, Pseudomonas exotoxin, alorin, saporin, modeccin, and gelanin. The polypeptide (e.g., antibody, or a binding fragment thereof), and the toxin can be linked in several ways. If the hybrid molecule is produced by expression of a fused gene, a peptide bond serves as the link between the toxin and the polypeptide.

Alternatively, the toxin and the polypeptide can be produced separately and later coupled (e.g., by means of a non-peptide covalent bond). For example, the covalent linkage may take the form of a disulfide bond. In this case, the nucleic acid molecule encoding the polypeptide can optionally contain an extra cysteine codon. The cysteine condon can be positioned so as to not interfere with the binding activity of the molecule. The toxin molecule can be derivatized with a sulfhydryl group reactive with the cysteine of the modified polypeptide. In the case of a peptide toxin, this optionally can be accomplished by inserting DNA encoding a cysteine codon into the nucleic acid molecule encoding the toxin. In another alternative, a sulfhydryl group, either by itself or as part of a cysteine residue, can be introduced into the polypeptide of the subject invention using solid phase polypeptide techniques.

Moreover, the polypeptides described herein can be combined with other well-known therapies already in use. The combination of the polypeptide described herein and one or more other therapeutic agents can provide a greater therapeutic effect than either agent alone, and preferably generate an additive or a synergistic effect with current treatments. For example, the polypeptide of the invention can be combined with other therapies targeting the IGF-IR, Her2 or other components in the IGF signaling network, including IGF-I, IGF-II, IGF binding proteins, such as anti-Her 2 monoclonal antibody herceptin, anti-IGF-IR monoclonal antibodies CP751, 871 (Pfizer), MK-0646 (Pierre-Fabre/Merck), AmG479 (Amgen), IMC-A12 (ImClone), R1507 (Hoffmann LaRoche), robatumumab (Schering-Plough), and cytokine immune enhancement therapy (interleukin (IL)-2, IL-12, CD40L+IL-12, IL-7, and interferons (IFNs)). Such therapies can be administered in the manner already in use for the known treatment providing a therapeutic effect. The polypeptide of the invention can be a neutralizing antibody against IGF-IR useful for cancer therapy. In an embodiment, the antibody (or binding fragment thereof) of the subject invention inhibits IGF-IR function and inhibits IGF-IR-mediated signaling. The antibody (or binding fragment thereof) of the subject invention has a high affinity for IGF-IR and is specific for IGF-IR.

In an embodiment, the antibody, or binding fragment thereof physically associates with other molecules (e.g., anti-IGF-IR antibodies, anti-Her2 antibodies) to inhibit IGF-IR- and Her2-mediated signaling. In other words, the polypeptide specifically binds, specifically reacts with, or specifically interacts with other target molecules (e.g. IGF-I, -II, IGF binding proteins). In an alternative embodiment, the polypeptide does not substantially physically associate with other molecules.

The epitopes recognized by the polypeptides described herein can be used as cancer vaccine immunogens, as active portions of cancer vaccine immunogens, and as targets for inhibitors of IGF signaling network. For example, the epitopes described herein (or polypeptides comprising the epitopes) can be used as targets to isolate antibodies that, other than those described herein, bind to the epitopes described herein. These antibodies can be used in the treatment and diagnosis of cancer.

While it is possible to administer (for example, as a vaccine) an epitope (or polypeptide comprising the epitope) that is recognized by the antibodies of the subject invention in a pure or substantially pure form, the epitope can be formulated into a pharmaceutical composition, formulation, or preparation. Accordingly, the disclosure encompasses a composition containing an epitope (or polypeptide comprising the epitope) recognized by the antibody described herein. The composition can further contain one or more pharmaceutically acceptable carriers (as described herein) and, optionally, other therapeutic ingredients. The composition comprising such epitope can be used therapeutically or to otherwise generate an immune response.

For example, a vaccine is provided to enhance the patient's own immune response to the antigens present due to tumorogenesis. Such vaccine, which acts as an immunogen, optionally can be a partially or substantially purified recombinant polypeptide containing the epitope or an analog thereof. The polypeptide comprising the epitope can be conjugated with one or more lipoproteins, administered in liposomal form, or with an adjuvant. Also encompassed by the disclosure are methods of developing vaccines or immunogenic compositions using the epitopes described herein.

The disclosure is also directed to methods of downregulating IGF-IR and inhibiting IGF-IR-mediated signaling in a mammal. The methods involve administering an effective amount of the polypeptide (e.g. the antibody or a binding fragment thereof that specifically binds to human IGF-IR), nucleic acid molecule that encodes the polypeptide, a vector comprising the nucleic molecule, a cell comprising the nucleic acid molecule and/or vector, or compositions comprising the foregoing, to the mammal, wherein cancer cell growth and cancer metastasis are reduced or inhibited. In one embodiment, the mammal is a human.

In one embodiment, the subject invention provides administering to a mammal a polypeptide (e.g. the antibody or a binding fragment thereof that specifically binds to human IGF-IR), a nucleic acid molecule, a vector containing the nucleic acid encoding the polypeptide, or a cell (e.g., a host cell) containing any of the above.

In one embodiment, the subject invention provides a method for treating tumor or cancer, comprising administering to a subject in need of such treatment an effective amount of an isolated antibody, or a binding fragment thereof, to a subject. In another embodiment, the subject invention embodies the administration of nucleic acid molecules, vectors, and host cells of the subject invention for tumor or cancer therapy. In a specific embodiment, the subject invention can be used to treat or ameliorate prostate cancer, breast cancer, liver cancer, and colon cancer.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "subject," as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

Vectors include, for example, nucleic acid vectors, such as naked DNA and plasmids, and viral vectors, such as retroviral vectors, parvovirus-based vectors (e.g., adenoviral-based vectors and adeno-associated virus (AAV)-based vectors), lentiviral vectors (e.g., Herpes simplex (HSV)-based vectors), and hybrid or chimeric viral vectors, such as an adenoviral backbone with lentiviral components (see, e.g., Zheng et al., Nat. Biotech., 18(2), 176-80 (2000); International Patent Application WO 98/22143; International Patent Application WO 98/46778; and International Patent Application WO 00/17376) and an adenoviral backbone with AAV components (see, e.g., Fisher et al., Hum. Gene Ther., 7, 2079-2087 (1996)), all of which are hereby incorporated by reference). Vectors and vector construction are known in the art (see, e.g., Sam brook et al., Molecular Cloning: A Laboratory Manual, 2d edition, Cold Spring Harbor Laboratory, NY (1989); and Ausubel et al., Current Protocols in Molecular Biology, Green Publishing Associates and John Wiley & Sons, New York, N.Y. (1994), both of which are hereby incorporated by reference).

The vector can contain any suitable promoter and other regulatory sequences (e.g., transcription and translation initiation and termination codons, which are specific to the type of host) to control the expression of the nucleic acid sequence encoding the polypeptide. The promoter can be a native or normative promoter operably linked to the nucleic acid molecule described above. The selection of promoters, including various constitutive and regulatable promoters, is within the skill of an ordinary artisan.

Examples of regulatable promoters include inducible, repressible, and tissue-specific promoters. Specific examples include viral promoters, such as adenoviral promoters and AAV promoters. Additionally, combining the nucleic acid described above with a promoter is within the skill in the art.

Cells (e.g., isolated host cells) containing the above-described polypeptide or nucleic acid molecule encoding the polypeptide, optionally in the form of a vector, are also provided by the disclosure. Any suitable cell can be used. Examples include host cells, such as *E. coli* (e.g., *E. coli* Tb-1, TG-2, DH5a, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic host cells include VERO, HeLa, 3T3, Chinese hamster ovary (CHO) cells, W138 BHK, COS-7, and MDCK cells. Alternatively, cells from a mammal, such as a human, to be treated in accordance with the methods described herein can be used as host cells.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., Molecular Biology: A Laboratory Manual, Cold Spring Harbor Laboratory, NY (1989); Davis et al., Basic Methods in Molecular Biology (1986); and Neumann et al., EMBO J. 1, 841 (1982), all of which are hereby incorporated by reference). In one embodiment, the cell containing the vector or nucleic acid molecule is transcribed and translated efficiently by the cell.

The nucleic acid molecules, vectors, cells, and polypeptides can be administered to a mammal alone, or in combination with a pharmaceutically acceptable carrier. By pharmaceutically acceptable is meant a material that is not biologically or otherwise undesirable (e.g., the material can be administered to a mammal, along with the nucleic acid, vector, cell, or polypeptide, without causing undesirable biological effects or interacting in a deleterious manner with other components of the pharmaceutical composition in which it is contained). The carrier is selected to minimize the degradation of the agent and to minimize adverse side effects in the mammal. The selection of carrier is well-known to one of ordinary skill in the art.

Suitable carriers and their formulations are described in Remington: The Science and Practice of Pharmacy (19th ed.) ed. A. R. Gennaro, Mack Publishing Company, Easton, Pa. (1995). Examples of pharmaceutical carriers include sterile water, saline, Ringer's solution, dextrose solution, and buffered solutions at physiological pH.

Typically, an appropriate amount of a pharmaceutically acceptable salt is used in the formulation to render the formulation isotonic. In one embodiment, the pH of the solution is from about 5 to about 8 (e.g., about 5.5, about 6, about 6.5, about 7, about 7.5, and ranges including any of these amounts therebetween), although pHs outside this range can be employed. In another embodiment, the pH is about 7 to about 7.5.

The pharmaceutical composition of the subject invention can also include sustained-release preparations, such as semipermeable matrices of solid hydrophobic polymers containing the polypeptide, which matrices are in the form of shaped articles (e.g., films, liposomes, or microparticles). It will be apparent to those persons skilled in the art that certain carriers may be more preferable depending upon, for instance, the route of administration and the concentration of composition being administered.

Examples of compositions (e.g., pharmaceutical compositions) containing the nucleic acid molecule, vector, cell, or polypeptide can include carriers, thickeners, diluents, buffers, preservatives, surface active agents and the like. The compositions can also include one or more active ingredients, such as anti-IGF-I, -II antibodies, chemotherapy drugs, and the like. The compositions described herein can be approved for use by the U.S. FDA or the equivalent in other countries. The composition (e.g., pharmaceutical composition) containing the nucleic acid molecule, vector, cell, or polypeptide can be administered in any suitable manner depending on whether local or systemic treatment is desired, and on the area to be treated.

If the composition is to be administered parenterally, the administration is generally by injection. Injectables can be prepared in conventional forms, either as liquid solutions or suspensions, solid forms suitable for being prepared as a solution or suspension prior to injection, or as emulsions. Additionally, parental administration can involve the preparation of a slow-release or sustained-release system, such that a constant dosage is maintained (see, e.g., U.S. Pat. No. 3,610,795, which is hereby incorporated by reference). Preparations for parenteral administration include sterile aqueous or nonaqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

The compositions can be in a form of acid- or base-addition salts, obtainable by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The nucleic acid molecules, vectors, or polypeptides can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

The exact amount of the compositions required to treat cancer may vary, depending on the species, age, gender, weight, and general conditions of the mammal, the particular polypeptide, nucleic acid, vector, or cell used, the route of administration, and whether other drugs are included in the regimen. Thus, it is not possible to specify an exact amount for every composition. However, an appropriate, suitable amount can be determined by one of ordinary skill in the art using only routine experimentation given the teachings herein. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days (or any suitable period of time to advance treatment). The composition can be administered immediately upon determination of cancer and continuously or intermittently administered.

The term "effective amount," as used herein, refers to an amount that is capable of treating or ameliorating a disease or condition or otherwise capable of producing an intended therapeutic effect. In an embodiment, an effective amount is an amount that is useful for treating or ameliorating tumor or cancer. In an embodiment, an effective amount enables an inhibition or reduction of cancer cell growth or metastasis in a subject. Effective dosages and schedules for administering the therapeutic agents and compositions described herein can be determined empirically, and making such determinations is routine to one of ordinary skill in the art.

The skilled artisan will understand that the dosage of the polypeptides varies, depending upon, for example, the route of administration, the particular polypeptide to be used, other drugs being administered, and the age, condition, gender and seriousness of the disease in the subject as described above. An effective dose of the polypeptide described herein generally ranges between about 1 µg/kg of body weight and 100 mg/kg of body weight. Examples of such dosage ranges are, e.g., about 1 µg-100 µg/kg, about 100 µg-1 mg/kg, about 1 mg/kg-10 mg/kg, or about 10 mg-100 mg/kg, once a month, a week, bi-weekly, daily, or two to four times daily.

Guidance in selecting appropriate doses for anti-IGF-IR antibodies, such as the polypeptides described herein, is found in the literature on therapeutic uses of antibodies (see, e.g., Handbook of Monoclonal Antibodies, Ferrone et al., eds., Noges Publications, Park Ridge, N.J., (1985); and Smith et al., Antibodies in Human Diagnosis and Therapy, Haber et al., eds., Raven Press, New York (1977), all of which are hereby incorporated by reference. A typical daily dosage of the polypeptide used might range from about 1 µg/kg to up to about 100 mg/kg of body weight or more per day, depending on the factors mentioned above. For example, the range can be from about 100 mg to about 1 g per dose. Nucleic acids, vectors, and host cells should be administered so as to result in comparable levels of production of polypeptides.

The disclosure also includes kits comprising the polypeptides, nucleic acid molecules, vectors, cells, epitopes, or compositions of the foregoing. The kits can include a separate container containing a suitable carrier, diluent, or excipient. The kits also can include an adjuvant, cytokine, antiviral agent, immunoassay reagents, PCR reagents, radiolabels, and the like. Additionally, the kits can include instructions for mixing or combining ingredients and/or administration.

The disclosure also provides a method of detecting IGF-IR in a mammal comprising contacting a sample obtained from the mammal with the polypeptide described herein. If an antigen is present in the mammal, to which the polypeptide can bind, a complex forms between the polypeptide and the antigen. Detection of the complex indicates the presence of elevated IGF-IR in the mammal.

The sample from the mammal can be of any suitable sample to detect the presence of IGF-IR. The complex can be detected by any suitable manner. The polypeptides described herein are utilizable as labeled molecules employed in radioimmunoassay (RIA) or enzyme immunoassay (EIA), particularly enzyme linked immunosorbent assay (ELISA), by introducing thereto radioactive substances such as 1125, 1131, H3 (tritium), C14, and the like; various enzyme reagents such as peroxidase (POX), chymotripsinogen, procarboxypeptidase, glyceraldehyde-3-phosphate dehydrogenase, amylase, phosphorylase, D-Nase, P-Nase, i3-galactosidase, glucose-6-phosphate dehydrogenase, ornithine decarboxylase, and the like. The radioactive substance can be introduced in a conventional manner. For example, the introduction of radioactive iodine, 1125, can be carried out by the oxidative ionization method using chloramine T (see, e.g., Hunter et al., Nature, 194, 495-496 (1962)) or by using the Bolten-Hunter reagent (1125-iodinated p-hydroxyphenyl propionic acid N-hydroxy-succinimide ester), which is hereby incorporated by reference.

The label for use in the method can be any suitable label known in the art, such as biotinylated proteins or peptides.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. An isolated polypeptide comprising an antibody or a binding fragment of the antibody, wherein the antibody or the binding fragment specifically binds to human insulin-like growth factor I receptor (IGF-IR), wherein the antibody or the binding fragment comprises a complementary-determining region (CDR) having an amino acid sequence selected from the group consisting of SEQ ID NO: 9, SEQ ID NO: 10, SEQ ID NO: 3, SEQ ID NO: 11, GTS, and SEQ ID NO: 4.

2. The isolated polypeptide according to claim 1, wherein CDR1 of a $V_H$ region of the antibody or the binding fragment comprises SEQ ID NO: 9, CDR2 of a $V_H$ region of the antibody or the binding fragment comprises SEQ ID NO: 10, and CDR3 of a $V_H$ region of the antibody or the binding fragment comprises SEQ ID NO: 3.

3. The isolated polypeptide according to claim 2, wherein a $V_H$ region of the antibody or the binding fragment comprises SEQ ID NO: 1.

4. The isolated polypeptide according to claim 2, wherein CDR1 of a $V_L$ region of the antibody or the binding fragment comprises SEQ ID NO: 11, CDR2 of a $V_L$ region of the antibody or the binding fragment comprises GTS, and CDR3 of a $V_L$ region of the antibody or the binding fragment comprises SEQ ID NO: 4.

5. The isolated polypeptide according to claim 4, wherein a $V_L$ region of the antibody or the binding fragment comprises SEQ ID NO: 2.

6. The isolated polypeptide according to claim 1, which specifically binds to human IGF-IR expressed on cancer cells.

7. The isolated polypeptide according to claim 1, which specifically binds to extracellular domain of human IGF-IR.

8. The isolated polypeptide according to claim 2, wherein the antibody is a monoclonal antibody.

9. The isolated polypeptide according to claim 1, wherein the antibody comprises an Fab, Fab', F(ab')$_2$, or scFv.

10. The polypeptide according to claim 1, wherein the antibody is a humanized antibody.

11. A pharmaceutical composition comprising an isolated polypeptide according to claim 1 and a pharmaceutically acceptable carrier.

12. The isolated polypeptide according to claim 1, comprising SEQ ID NO: 3.

13. The isolated polypeptide according to claim 1, comprising SEQ ID NO: 4.

* * * * *

UNITED STATES PATENT AND TRADEMARK OFFICE
CERTIFICATE OF CORRECTION

PATENT NO. : 8,444,982 B2  
APPLICATION NO. : 12/955627  
DATED : May 21, 2013  
INVENTOR(S) : Mei-Yun Zhang It is certified that error appears in the above-identified patent and that said Letters Patent is hereby corrected as shown below:

In the Specification

Column 4,
Line 39, "a VI region" should read --a $V_L$ region--.

Signed and Sealed this
Twenty-fourth Day of September, 2013

Teresa Stanek Rea
*Deputy Director of the United States Patent and Trademark Office*

SEQUENCE LISTING

<160> NUMBER OF SEQ ID NOS: 15

<210> SEQ ID NO 1
<211> LENGTH: 124
<212> TYPE: PRT

<213> ORGANISM: Artificial Sequence
<220> FEATURE:
<223> OTHER INFORMATION: amino acid sequence of a VH region of the H10
      antibody

<400> SEQUENCE: 1

Glu Val Gln Leu Leu Glu Ser Gly Ala Glu Val Lys Arg Pro Gly Ser
1               5                   10                  15

Ser Val Arg Val Ser Cys Gln Val Ser Gly Tyr Ser Phe Thr Ala Tyr
            20                  25                  30

Tyr Val Ser Trp Val Arg Gln Thr Pro Gly His Gly Leu Glu Trp Met
        35                  40                  45

Gly Gly Ile Asn Pro Asp Asn Gly Gly Asn Asn Tyr Ala Gln Lys Phe
    50                  55                  60

His Gly Arg Val Thr Phe Ile Ala Asp Glu Ser Thr Arg Thr Val His
65                  70                  75                  80

Met Glu Leu Arg Ser Leu Arg Ser Glu Asp Thr Ala Val Tyr Phe Cys
                85                  90                  95

Ala Lys Ser Thr Ser Tyr Asp Tyr Asp Gly Tyr Trp Tyr Phe Asp Val
            100                 105                 110

Trp Gly Gln Gly Thr Ala Val Thr Val Phe Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: amino acid sequence of a VL region of the H10
      antibody

<400> SEQUENCE: 2

Glu Leu Gln Met Thr Gln Ser Pro Ser Ser Val Ser Ala Ser Val Gly
1               5                   10                  15

Asp Arg Val Thr Ile Thr Cys Arg Ala Ser Ser Ser Val Ser Tyr Leu
            20                  25                  30

Ala Trp Tyr Gln Gln Lys Pro Gly Lys Ala Pro Lys Leu Leu Leu Asn
        35                  40                  45

Gly Thr Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Ser Tyr Pro Phe Thr
                85                  90                  95

Phe Gly Gly Gly Thr Lys Val Glu Ile Lys Arg
            100                 105

<210> SEQ ID NO 3
<211> LENGTH: 16
<212> TYPE: PRT
<213> ORGANISM: Artificial Sequence
<220> FEATURE:
<223> OTHER INFORMATION: amino acid sequence of an H3 region of the H10
      antibody

<400> SEQUENCE: 3

Ala Lys Ser Thr Ser Tyr Asp Tyr Asp Gly Tyr Trp Tyr Phe Asp Val
1               5                   10                  15

<210> SEQ ID NO 4
<211> LENGTH: 9

```
<212> TYPE: PRT
<213> ORGANISM: Artificial Sequence
<220> FEATURE:
<223> OTHER INFORMATION: amino acid sequence of an L3 region of the H10
      antibody

<400> SEQUENCE: 4

Gln Gln Arg Ser Ser Tyr Pro Phe Thr
1               5

<210> SEQ ID NO 5
<211> LENGTH: 372
<212> TYPE: DNA
<213> ORGANISM: Artificial Sequence
<220> FEATURE:
<223> OTHER INFORMATION: nucleic acid sequence of a VH region of the H10
      antibody

<400> SEQUENCE: 5
gaggtgcagc tgctcgagtc tggggctgag gtgaagaggc ctgggtcctc ggtgagagtc        60
tcctgccaag tttctggtta ctcattcact gcctactacg tcagttgggt gcgacagacc      120
cctggacacg gcttgagtg gatgggaggg attaatcctg acaatggtgg taacaactac       180
gcacagaagt tcacggccg agtgacattt atcgccgacg agtccacgag acagtccac        240 atggaactgc gcagcctgag atctgaggac acggccgtct attttgtgc aaagtcaacc       300 tcctatgatt acgacggtta ctggtacttc gatgtctggg gccaagggac cgcggtcacc      360
gtcttctcct ca                                                          372

<210> SEQ ID NO 6
<211> LENGTH: 320
<212> TYPE: DNA
<213> ORGANISM: Artificial Sequence
<220> FEATURE:
<223> OTHER INFORMATION: nucleic acid sequence of a VL region of the H10
      antibody

<400> SEQUENCE: 6
gagctccaga tgacccagtc tccatcttcc gtgtctgcat ctgtcggaga cagagtcacc        60
atcacttgtc gggcgagttc aagtgtaagt tacttagcct ggtatcagca gaaaccaggg      120
aaagccccta agctcctgat caatggcacg tccagtttgc aaagtggggt cccatcaagg      180
ttcagcggca gtggatctgg gacagatttc actctcacca tcagcagcct gcagcctgaa      240
gatttgcgac ttactattgt cagcaaagga gtagttaccc attcacgttc ggcggaggga      300
ccaaggtgga gatcaaacga                                                  320

<210> SEQ ID NO 7
<211> LENGTH: 48
<212> TYPE: DNA
<213> ORGANISM: Artificial Sequence
<220> FEATURE:
<223> OTHER INFORMATION: nucleic acid sequence of an H3 region of the
      H10 antibody

<400> SEQUENCE: 7
gcaaagtcaa cctcctatga ttacgacggt tactggtact tcgatgtc                    48

<210> SEQ ID NO 8
<211> LENGTH: 27
<212> TYPE: DNA
<213> ORGANISM: Artificial Sequence
<220> FEATURE:
<223> OTHER INFORMATION: nucleic acid sequence of an L3 region of the
      H10 antibody
```

```
<400> SEQUENCE: 8
cagcaaagga gtagttaccc attcacg                                              27

<210> SEQ ID NO 9
<211> LENGTH: 8
<212> TYPE: PRT
<213> ORGANISM: Artificial Sequence
<220> FEATURE:
<223> OTHER INFORMATION: amino acid sequence of CDR1 of a VH region of
      the H10 antibody

<400> SEQUENCE: 9

Gly Tyr Ser Phe Thr Ala Tyr Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: amino acid sequence of CDR2 of a VH region of
      the H10 antibody

<400> SEQUENCE: 10

Ile Asn Pro Asp Asn Gly
1               5

<210> SEQ ID NO 11
<211> LENGTH: 6
<212> TYPE: PRT
<213> ORGANISM: Artificial Sequence
<220> FEATURE:
<223> OTHER INFORMATION: amino acid sequence of CDR1 of a VL region of
      the H10 antibody

<400> SEQUENCE: 11

Ser Ser Val Ser Tyr Leu
1               5

<210> SEQ ID NO 12
<211> LENGTH: 24
<212> TYPE: DNA
<213> ORGANISM: Artificial Sequence
<220> FEATURE:
<223> OTHER INFORMATION: nucleic acid sequence of CDR1 of a VH region of
      the H10 antibody

<400> SEQUENCE: 12
ggttactcat tcactgccta ctac                                                 24

<210> SEQ ID NO 13
<211> LENGTH: 13
<212> TYPE: DNA
<213> ORGANISM: Artificial Sequence
<220> FEATURE:
<223> OTHER INFORMATION: nucleic acid sequence of CDR2 of a VH region of
      the H10 antibody

<400> SEQUENCE: 13
attaatcctg aca                                                             13

<210> SEQ ID NO 14
<211> LENGTH: 15
<212> TYPE: DNA
<213> ORGANISM: Artificial Sequence
<220> FEATURE:
<223> OTHER INFORMATION: nucleic acid sequence of CDR1 of a VL region of
``` the H10 antibody

<400> SEQUENCE: 14
tcaagtgtaa gttac                    15

<210> SEQ ID NO 15
<211> LENGTH: 1367
<212> TYPE: PRT
<213> ORGANISM: Homo sapiens

<400> SEQUENCE: 15

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
                325                 330                 335

Lys Thr Lys Thr Ile Asp Ser Val Thr Ser Ala Gln Met Leu Gln Gly
            340                 345                 350

-continued

```
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
                420                 425                 430
Asp Trp Asp His Arg Asn Leu Thr Ile Lys Ala Gly Lys Met Tyr Phe
                435                 440                 445
Ala Phe Asn Pro Lys Leu Cys Val Ser Glu Ile Tyr Arg Met Glu Glu
                450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                485                 490                 495
Ser Thr Thr Thr Ser Lys Asn Arg Ile Ile Ile Thr Trp His Arg Tyr
                500                 505                 510
Arg Pro Pro Asp Tyr Arg Asp Leu Ile Ser Phe Thr Val Tyr Tyr Lys
                515                 520                 525
Glu Ala Pro Phe Lys Asn Val Thr Glu Tyr Asp Gly Gln Asp Ala Cys
                530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
                580                 585                 590
His Ile Arg Gly Ala Lys Ser Glu Ile Leu Tyr Ile Arg Thr Asn Ala
                595                 600                 605
Ser Val Pro Ser Ile Pro Leu Asp Val Leu Ser Ala Ser Asn Ser Ser
610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
                660                 665                 670
Tyr Ala Asp Gly Thr Ile Asp Ile Glu Glu Val Thr Glu Asn Pro Lys
                675                 680                 685
Thr Glu Val Cys Gly Gly Glu Lys Gly Pro Cys Cys Ala Cys Pro Lys
690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735
Arg Lys Arg Arg Asp Val Met Gln Val Ala Asn Thr Thr Met Ser Ser
                740                 745                 750
Arg Ser Arg Asn Thr Thr Ala Ala Asp Thr Tyr Asn Ile Thr Asp Pro
                755                 760                 765
Glu Glu Leu Glu Thr Glu Tyr Pro Phe Phe Glu Ser Arg Val Asp Asn
770                 775                 780
```

```
Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
```

-continued

```
                1190                  1195                      1200
Glu Ile Ala Thr Leu Ala Glu Gln Pro Tyr Gln Gly Leu Ser Asn
    1205                 1210                 1215

Glu Gln Val Leu Arg Phe Val Met Glu Gly Gly Leu Leu Asp Lys
    1220                 1225                 1230

Pro Asp Asn Cys Pro Asp Met Leu Phe Glu Leu Met Arg Met Cys
    1235                 1240                 1245

Trp Gln Tyr Asn Pro Lys Met Arg Pro Ser Phe Leu Glu Ile Ile
    1250                 1255                 1260

Ser Ser Ile Lys Glu Glu Met Glu Pro Gly Phe Arg Glu Val Ser
    1265                 1270                 1275

Phe Tyr Tyr Ser Glu Glu Asn Lys Leu Pro Glu Pro Glu Glu Leu
    1280                 1285                 1290

Asp Leu Glu Pro Glu Asn Met Glu Ser Val Pro Leu Asp Pro Ser
    1295                 1300                 1305

Ala Ser Ser Ser Ser Leu Pro Leu Pro Asp Arg His Ser Gly His
    1310                 1315                 1320

Lys Ala Glu Asn Gly Pro Gly Pro Gly Val Leu Val Leu Arg Ala
    1325                 1330                 1335

Ser Phe Asp Glu Arg Gln Pro Tyr Ala His Met Asn Gly Gly Arg
    1340                 1345                 1350

Lys Asn Glu Arg Ala Leu Pro Leu Pro Gln Ser Ser Thr Cys
    1355                 1360                 1365
```